United States Patent [19]

Kleinberger

[11] 4,259,353
[45] Mar. 31, 1981

[54] INFUSION SOLUTIONS FOR THE TREATMENT OF HEPATIC ENCEPHALOPATHY AND METHOD OF USING THEM

[75] Inventor: Günter Kleinberger, Vienna, Austria

[73] Assignee: Leopold & Co., Chem. Pharm. Fabrik Gesellschaft m. b. H., Graz, Austria

[21] Appl. No.: 957,204

[22] Filed: Nov. 3, 1978

[30] Foreign Application Priority Data

Nov. 9, 1977 [DE] Fed. Rep. of Germany ....... 2750159

[51] Int. Cl.³ .......................................... A61K 31/195
[52] U.S. Cl. ................................................... 424/319
[58] Field of Search ......................................... 424/319

[56] References Cited

U.S. PATENT DOCUMENTS 3,764,703 10/1973 Bergström et al. ................ 424/319
3,832,465 8/1974 Ghadimi ............................. 424/177
3,950,529 4/1976 Fischer et al. ................. 424/319 X

OTHER PUBLICATIONS

Chem. Abst. – vol. 773, No. 143772d, Seydel et al., 1972.
Chem. Abst. – vol. 82, No. 168449v, Glaubitt et al., 1975.
Chem. Abst. – vol. 73, No. 85550j – Lacy, 1970.

Primary Examiner—Frederick E. Waddell
Attorney, Agent, or Firm—Wenderoth, Lind & Ponack

[57] ABSTRACT

Infusion solution for the treatment of human patients with heptic encephalopathy which consists essentially of a sterile aqueous solution of L-valine and has a pH-value of 7,4 to 7,5. This infusion solution when intravenously administered to patients in an amount of 20–85 mg/kg of body weight per hour influences hepatic encephalopathy in a very advantageous manner.

2 Claims, No Drawings

INFUSION SOLUTIONS FOR THE TREATMENT OF HEPATIC ENCEPHALOPATHY AND METHOD OF USING THEM

It is known that in patients with hepatic encephalopathy, especially those in praecoma or coma hepaticum, the content of the branched amino acids valine, leucine and isoleucine is lower than normal and the content of the aromatic amino acids phenylalanine, tyrosine and tryptophane is higher than normal, see Fisher et al., Am. J. Surg, volume 127, page 40 (1974).

Since such patients also require parenteral feeding, it has been proposed according to U.S. Pat. No. 3,950,529 to use nutrient solutions which contain at least the essential amino acids and in which very specific relationships between the branched-chain amino acids and the aromatic amino acids must be maintained, the content of tryptophane and of phenylalanine being limited in particular. By this means, excessive tryptophane transport to the brain is said to be prevented and it is said to be ensured that too high a phenylalanine content does not arise in the plasma.

In the paper by E. Fisher et al., Surgery Vol. 80, No. 1, 77-91, 1976, it was finally pointed out that the degree of hepatic encephalopathy is decisively dependent on the factor of the concentration of the branched amino acids valine, leucine and isoleucine to that of the aromatic amino acids phenylalanine, tyrosine and tryptophane. It is suggested that the branched chain amino acids are competing with the aromatic amino acids for entry across the blood brain barrier and a higher dosage level of branched chain amino acids leads to a lower concentration of aromatic amino acids in the brain. It is presumed, that by this action the brain neurotransmitter profile, which is deranged in hepatic encephalopathy, can be improved. It is therefore pointed out that with nutrient solutions which are of a composition calculated so that it aims to normalize the amino acid level in the plasma, an amelioration of the encephalopathy is also achieved although the solutions also contain some amount of aromatic amino acids.

In practice, however, it has been found that an improvement in the amino acid level is achieved only very slowly with such solutions.

Surprisingly, it has now been possible to find that hepatic encephalopathy can be influenced in a very advantageous manner if considerably higher doses only of the branched chain amino acid L-valine, are administered, the doses being from about 20 to 85 mg/kg of body weight per hour. The administration of such a high dose of valine is possible only if this is separated from the feeding of the patient for example with a solution according to U.S. Pat. No. 3,950.529 and is administered intravenously in the form of an infusion which contains only L-valine on its own but does not contain any other amino acid.

The administration of L-valine according to the invention surprisingly is accompanied by diminution of ammonia in tissue. In hepatic encephalopathy the ammonia-level in tissue is considerably increased and since ammonia acts strongly cytotoxic, the lowering effect of L-valine leads to a immediate and remarkable reduction of incidence and severity of hepatic encephalopathy. The reduction of ammonia-level in tissue is only possible with L-valine, but not with leucine or isoleucine. The administration of these latter branched chain amino acids in such a high dosage level would lead to the formation of toxic keto-compounds in the human body. Further L-valine is able to improve the energy supply of the body, which is low in hepatic encephalopaty due to interruption of the citric acid cycle.

Accordingly, the present invention relates to an intravenous infusion solution for the treatment of human patients with hepatic encephalopathy consisting essentially of a sterile aqueous solution of L-valine said solution having a pH-value within the physiologically acceptable range of 7.0 to 7.5, which had been adjusted by neutralization with a base acceptable for infusion.

Preferably this infusion solution has a concentration of L-valine of 2-5 g/100 ml solution. This solution may also contain a sugar or a sugar alcohol, as for example xylit, their concentration is limited to 5% per weight as a maximum.

In order to prepare this infusion solution, valine is simply dissolved in water and the solution is neutralized with a water-soluble base acceptable for infusions, such as, for example, sodium hydroxide solution, or organic amines, such as, for example, dimethylaminoethanol, diethylaminoethanol or aminoethanol, until the pH has been adjusted to the physiological pH value of about 7.0 to 7.5, preferably 7.4. The sugars or sugar-alcohols, which may be present in concentrations up to the limit of 5%, can be incorporated in the aqueous solution before or after the valine is added. Xylitol is particularly suitable for this purpose.

The present invention provides also a method of treating hepatic encephalopathy, especially praecoma or coma hepaticum in human patients by intravenously infusing said patient with the infusion solution according to the present invention. Suitable amounts are 20-85 mg/kg of body weight of L-valine per hour, whereby the suitable amount within the range is to be chosen in dependance of the severity of the symptoms of hepatic encephalopathy.

It is an advantage of the present invention that by administering it on its own, the supply of valine during the administration can be suited to the requirements of the patient. Thus, for example, a relatively high dose, for example of about 80 mg/kg of body weight per hour, can be administered for the first few hours and, after a relatively high level in the plasma has been reached, the dose can be reduced somewhat, for example to about 20 to 30 mg/kg. During administration of the valine, the patient is fed parenterally only.

Example:

12.5 g of valine are dissolved in water and the solution is brought towards neutral with 7.2 ml of a 0.1 N sodium hydroxide solution and the pH is adjusted to the physiological pH value of 7.4. The mixture is then made up of 250 ml with water ad infundi. Infusion volumes of 100 and 500 ml can also be prepared in the same way.

What we claim is:

1. A method of treating hepatic encephalopathy in human patients comprising intravenously infusing a solution consisting essentially of a sterile aqueous solution of L-valine as the sole amino acid, said solution having a pH-value within the physiologically acceptable range of 7.0 to 7.5 which has been adjusted by a base acceptable for infusion, and said solution having a concentration of L-valine of 2-5 g/100 ml of the solution.

2. A method according to claim 1, in which said L-valine is infused in an amount of 20 to 85 mg/kg of body weight per hour.

* * * * *